(12) United States Patent
Robbins et al.

(10) Patent No.: US 10,695,287 B2
(45) Date of Patent: Jun. 30, 2020

(54) AMPK AGONIST TOPICAL MEDICATION FOR THE TREATMENT OF CERTAIN SPECIFIC MEDICAL CONDITIONS, METHODS OF USE THEREOF AND WOUND DRESSING EMPLOYING THE SAME

(71) Applicant: CERSCI THERAPEUTICS, INC., Dallas, TX (US)

(72) Inventors: Dennis I. Robbins, Dallas, TX (US); David H. Hitt, II, Dallas, TX (US)

(73) Assignee: CerSci Therapeutics, Inc., Dallas, TX (US)

( * ) Notice: Subject to any disclaimer, the term of this patent is extended or adjusted under 35 U.S.C. 154(b) by 0 days.

(21) Appl. No.: 16/119,024

(22) Filed: Aug. 31, 2018

(65) Prior Publication Data

US 2018/0369133 A1  Dec. 27, 2018

Related U.S. Application Data

(63) Continuation of application No. 15/354,372, filed on Nov. 17, 2016, now abandoned.

(60) Provisional application No. 62/256,402, filed on Nov. 17, 2015.

(51) Int. Cl.
| | |
|---|---|
| A61K 9/00 | (2006.01) |
| A61K 9/70 | (2006.01) |
| A61K 45/06 | (2006.01) |
| A61K 9/06 | (2006.01) |
| A61K 33/38 | (2006.01) |
| A61K 31/05 | (2006.01) |
| A61K 31/7036 | (2006.01) |
| A61K 31/18 | (2006.01) |
| A61M 35/00 | (2006.01) |
| A61N 1/04 | (2006.01) |
| A61N 1/36 | (2006.01) |

(52) U.S. Cl.
CPC .......... *A61K 9/0009* (2013.01); *A61K 9/0014* (2013.01); *A61K 9/06* (2013.01); *A61K 9/703* (2013.01); *A61K 9/7084* (2013.01); *A61K 31/05* (2013.01); *A61K 31/18* (2013.01); *A61K 31/7036* (2013.01); *A61K 33/38* (2013.01); *A61K 45/06* (2013.01); *A61M 35/003* (2013.01); *A61N 1/0432* (2013.01); *A61N 1/0448* (2013.01); *A61N 1/0456* (2013.01); *A61N 1/36021* (2013.01)

(58) Field of Classification Search
CPC .. A61K 2300/00; A61K 31/522; A61K 31/14; A61K 31/52; A61K 31/662; A61K 31/675; A61K 31/7072; A61K 31/7125; A61K 45/06; A61K 31/375; A61K 33/10; A61K 33/42; A61K 35/32; A61K 31/7052; A61K 31/7056; A61K 31/706; A61K 31/7064; A61K 31/7076; A61K 31/728; A61K 9/0014; A61K 31/05; A61K 31/10; A61K 31/155; A61K 31/167; A61K 31/192; A61K 31/4152; A61K 31/4439; A61K 31/445; A61K 31/7004; A61K 31/726; A61L 26/0085; A61L 2300/254; A61L 2300/418; A61L 24/0015; A61L 24/0036; A61L 24/102; A61L 24/104; A61L 26/0066
See application file for complete search history.

(56) References Cited

U.S. PATENT DOCUMENTS

| | | | | |
|---|---|---|---|---|
| 4,772,591 | A | * 9/1988 | Meisner | A61K 31/7004 424/602 |
| 9,125,911 | B2 | * 9/2015 | Johnson | A61K 31/522 |
| 2011/0021964 | A1 | 1/2011 | Larsen et al. | |
| 2014/0186306 | A1 | 7/2014 | Plante et al. | |

FOREIGN PATENT DOCUMENTS

| | | | |
|---|---|---|---|
| WO | 2014052640 A1 | 4/2014 | |
| WO | WO2014/052640 A1 * | 4/2014 | ........... A61K 31/155 |

* cited by examiner

*Primary Examiner* — Audrea B Coniglio
(74) *Attorney, Agent, or Firm* — Saul Ewing Arnstein & Lehr LLP; Domingos J. Silva; Dennis Ostrovsky

(57) ABSTRACT

A topical medication including a therapeutically effective amount of an AMPK (adenosine monophosphate-activated protein kinase) agonist for use in the treatment of one or more the human or animal medical conditions. The medical conditions include, but are not limited to: shingles (herpes zoster), post-herpetic neuralgia (PHN), gout, migraine, trigeminal neuralgia, Complex Regional Pain Syndrome (CRPS), diabetic neuropathy, peripheral neuropathy, rheumatoid arthritis, insect-related wheals, urushiol-related rash, psoriasis, herpes simplex, atopic dermatitis (eczema), contact dermatitis, allergic dermatitis, neurotrophic ulcers, first- and second-degree burns (e.g., sunburn and chemical), fibromyalgia, rubeola, and acne. Also disclosed are a method of employing the composition and a wound dressing incorporating a therapeutically effective amount of an AMPK agonist in combination with an antimicrobial agent.

16 Claims, 4 Drawing Sheets

AMPK AGONIST TOPICAL MEDICATION FOR THE TREATMENT OF CERTAIN SPECIFIC MEDICAL CONDITIONS, METHODS OF USE THEREOF AND WOUND DRESSING EMPLOYING THE SAME

CROSS-REFERENCE TO RELATED APPLICATION

This application is a continuation of, and claims priority to, U.S. patent application Ser. No. 15/354,372, filed Nov. 17, 2016, which claims priority under 35 U.S.C. § 119(e) to U.S. Provisional Patent Application No. 62/256,402, filed Nov. 17, 2015, all of which applications are incorporated herein by reference in their entireties.

TECHNICAL FIELD

This application is directed, in general, to the pharmacological treatment of pain, itching, and inflammation associated with certain medical conditions, by use of a topical medication and a wound dressing comprising specific agents for the mitigation of pain and mitigation of infection.

BACKGROUND

Pain describes a sensation affecting one or more parts of a human or animal body, resulting in distress and a desire to eliminate or mitigate the sensation and/or its source. According to the definition provided by the International Association for the Study of Pain, "[p]ain is an unpleasant sensory and emotional experience associated with actual or potential tissue damage, or described in terms of such damage" (see, International Association for the Study of Pain: Pain Definitions," Retrieved 12 Jan. 2015, derived from Bonica, "The need of a taxonomy," Pain; 6(3):247-8. doi:10.1016/0304-3959(79)90046-0. PMID 460931) (1979).

5' adenosine monophosphate-activated protein kinase, or "AMPK," is an enzyme that plays a role in cellular energy homeostasis (see, e.g., http://en dot wikipedia dot org/wiki/AMP-activated_protein_kinase). AMPK is expressed in various types of tissue, including the liver, brain, and skeletal muscle. AMPK activation results in the stimulation of hepatic fatty acid oxidation and ketogenesis, inhibition of cholesterol synthesis, lipogenesis, and triglyceride synthesis, inhibition of adipocyte lipolysis and lipogenesis, stimulation of skeletal muscle fatty acid oxidation and muscle glucose uptake, and modulation of insulin secretion by pancreatic beta-cells (supra, and Winder, et al., "AMP-Activated Protein Kinase, a Metabolic Master Switch: Possible Roles in Type 2 Diabetes," Am. J. Physiol. 277 (1 Pt 1): E1-10. PMID 10409121, July 1999). Various research efforts have indicated a promising role for AMPK activation in the mitigation of pain, including neuropathic pain and nociceptive pain (see, Price, et al., "AMPK: An Emerging Target for Modification of Injury-Induced Pain Plasticity," Neurosci. Lett.; 557 Pt A:9-18. doi: 10.1016/j.neulet.2013.06.060. Epub 2013 Jul. 3 2013 Dec. 17, and, Tillu, et al., "Resveratrol Engages AMPK to Attenuate ERK and mTOR Signaling in Sensory Neurons and Inhibits Incision-Induced Acute and Chronic Pain," J. Mol. Pain 8:5. doi: 10.1186/1744-8069-8-5, 2012 Jan. 23). In this research, the topical administration of AMPK activators, also called agonists, e.g., resveratrol, has shown efficacy in mitigation of pain in an animal model (rodents).

SUMMARY

One aspect provides a topical medication. In one embodiment, the medication includes: (1) an AMPK agonist and (2) at least one inactive ingredient configured to mix with the AMPK agonist to form the topical medication.

Another aspect provides a method of applying a medication topically. In one embodiment, the method includes: (1) preparing the medication by mixing an AMPK agonist with at least one inactive ingredient configured to mix with the AMPK agonist to form the topical medication and (2) placing the medication in contact with skin.

Yet another aspect provides an iontophoretic transdermal system. In one embodiment, the system includes: (1) an AMPK agonist and (2) a Transcutaneous Electrical Nerve Stimulation (TENS) device having an anode and cathode and a controller coupled thereto, the medication associated with one of the anode and the cathode, the controller configured to control the anode and the cathode to conduct electrical neuromodulation therapy and increase a topical application rate of the medication.

Still another aspect provides an iontophoretic transdermal method. In one embodiment, the method includes: (1) associating a medication including an AMPK agonist with a TENS device, (2) topically applying a therapeutically effective amount of the medication, (3) employing the TENS device to apply the medication iontophoretically and (4) employing the TENS device to perform electrical neuromodulation therapy.

BRIEF DESCRIPTION

Reference is now made to the following descriptions taken in conjunction with the accompanying drawings, in which.

DETAILED DESCRIPTION

Figure 1:
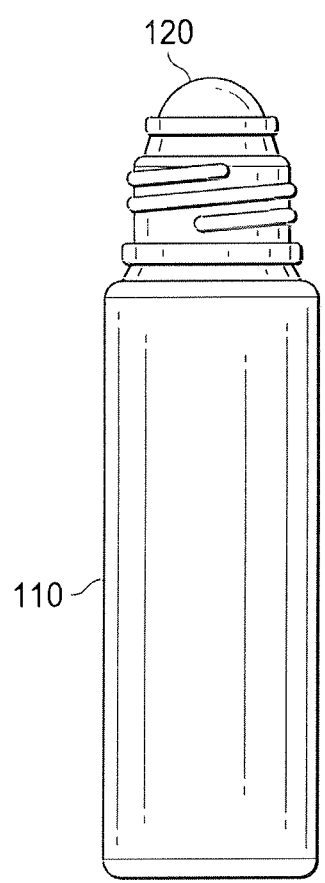
FIG. 1 is an elevational view of one embodiment of a roll-on applicator.

Disclosed herein are various ways to treat various medical conditions via topical administration of a therapeutically effective amount of AMPK activator(s), e.g., resveratrol. Specific disease conditions addressed disclosed herein include: shingles (herpes zoster), post-herpetic neuralgia (PHN), gout, migraine (when applied topically to the facial region near the ophthalmic, maxillary and/or mandibular branches), trigeminal neuralgia, CRPS (Complex Regional Pain Syndrome, also known as Reflexive Sympathetic Dystrophy), diabetic neuropathy, peripheral neuropathy, rheumatoid arthritis, insect-related wheals, urushiol-related rash (e.g., poison ivy), psoriasis, herpes simplex, atopic dermatitis (eczema), contact dermatitis, allergic dermatitis, neurotrophic ulcers, first- and second-degree burns (e.g., sunburn and chemical), fibromyalgia, rubeola, and acne.

Various aspects of the disclosure herein include an AMPK agonist topical medication for the treatment of certain specific medical conditions, methods of using the topical medication and a wound dressing employing the topical medication. The topical medication may be formulated in the form of a cream or a gel, with the inclusion of various inactive ingredients, including emulsifiers, moisturizers, and other ingredients intended to optimize the ease of topical application of the medication, and address aesthetic issues, including texture, viscosity, and scent.

The wound dressing described herein includes a therapeutically effective amount of a topical AMPK agonist, in combination with an antimicrobial agent. A wound dressing is intended for the treatment of various injuries and medical conditions. Synergistic benefit is expected to be achieved by incorporating the AMPK agonist in the dressing; pain resulting from the injury or condition could be mitigated, and by incorporating an antimicrobial agent, infection is expected to be suppressed. The suppression of infection is expected to result in less frequent changes of the wound dressing, and less pain and distress to the patient. Silver has been found to be particularly effective as an antimicrobial agent when incorporated into wound dressings. The silver ion Ag+ is bioactive, and in sufficient concentration, it readily kills bacteria (see, e.g., http://en dot wikipedia dot org/wiki/Medical uses of silver). A wound dressing incorporating silver as an antibacterial agent, in combination with an AMPK agonist for reduction of pain is expected to be particularly effective in promoting healing and reducing distress to the patient.

Also described herein is the use of a therapeutically effective amount of a topical AMPK agonist in combination with electrical neuromodulation therapy for the mitigation of pain. Examples of electrical neuromodulation therapy treatment include use a TENS device (see, e.g., http://en.wikipedia.org/wiki/Transcutaneous electrical nerve stimulation) for the treatment of subcutaneous pain, including muscle and joint pain and spasms, and the use of an electrical stimulation device worn on the forehead for the treatment of migraine. Synergistic effects are expected to result from the combination of the pain relief achieved through the use of the topical AMPK agonist, and the use of electrical neuromodulation therapy. In one embodiment, the electrical neuromodulation therapy comprises an active (closed-loop) feedback mechanism in which peripheral nerve signals are monitored, and the electrical signal therapy is automatically adjusted, in combination with the use of the topical AMPK agonist to maximize the pain mitigation effects.

Further described herein are application devices and methods for a therapeutically effective amount of a topical AMPK agonist. In one embodiment, roll-on application of the medication can be achieved by the use of a roller attached to the dispensing end of a container (FIG. 1) of the medication.

In one embodiment, the composition includes a therapeutically effective amount of an AMPK agonist for use as a topical medication for the treatment of one or more of the following human medical conditions: shingles (herpes zoster), post-herpetic neuralgia (PHN), gout, migraine (when applied topically to the facial region near the ophthalmic, maxillary and/or mandibular branches), trigeminal neuralgia, CRPS (Complex Regional Pain Syndrome, also known as Reflexive Sympathetic Dystrophy), diabetic neuropathy, peripheral neuropathy, rheumatoid arthritis, insect-related wheals, urushiol-related rash (e.g., poison ivy), psoriasis, herpes simplex, atopic dermatitis (eczema), contact dermatitis, allergic dermatitis, neurotrophic ulcers, first- and second-degree burns (e.g., sunburn and chemical), fibromyalgia, rubeola, acne, carpal tunnel syndrome, joint deterioration. In a specific embodiment, the composition is intended for use for the treatment of neuropathic, inflammatory, or nociceptive pain. In another specific embodiment, the composition is intended for use for the treatment of itching. In yet another specific embodiment, the composition is combined with one or more analgesic, antipruritic, and/or anti-inflammatory agents. In a more specific embodiment, the analgesic, antipruritic, and/or anti-inflammatory agent(s) include one or more of the following: methyl salicylate, trolamine salicylate, menthol, camphor, lidocaine, benzocaine, dibucaine, prilocaine, capsaicin, diclofenac sodium gel, hydrocortisone, clobetasol, diphenhydramine, ibuprofen, and ketoprofen. In still another specific embodiment, the AMPK agonist consists of one or more the following: metformin, 5-Aminoimidazole-4-carboxamide ribonucleotide (AICAR), berberine, epigallocatechin-3-gallate, (EGCG), carnitine, R-Lipoic acid, quercetin, glucosamine, curcumin, anthocyanins, cannabinoids, genistein, astragalus, reishi, rooibos, creatine, gynostemma, apigenin, hydroxytyrosol, baicalin.

For purposes of this particular disclosure, "AMPK agonist" and "AMPK activator" are defined as including all known and later-discovered and later-developed AMPK agonists, except resveratrol. Resveratrol is excluded from the definition of "AMPK agonist" and "AMPK activator." "AMPK agonist," "AMPK activator," non-resveratrol AMPK agonist" and "non-resveratrol AMPK activator" are completely synonymous. A medication having multiple AMPK agonists is still regarded as falling within the definition of AMPK agonist, even though it may also include resveratrol.

In yet still another specific embodiment, the composition includes one or more inactive ingredients. In a more specific embodiment, the inactive ingredient(s) include one or more of the following: water, mineral oil, glycerin, stearic acid, phenoxyethanol, panthenol, cetearyl alcohol, sodium hydroxide, sodium citrate, citric acid, and ethylparaben. In still yet another specific embodiment, the composition is combined with dimethyl sulfoxide or pluronic lecithin organogel for improved transdermal absorption efficacy. In yet still another embodiment, the topical medication is intended for use in the treatment of non-human animals (e.g., dogs, horses, or cats), rather than humans.

In one embodiment, the composition includes a therapeutically effective amount of an AMPK agonist for use as a topical medication for the treatment of pain resulting from physical injury, including but not limited to: repetitive motion, blunt force trauma, laceration, abrasion, thermal or chemical burns, frostbite, and puncture.

Figure 4:
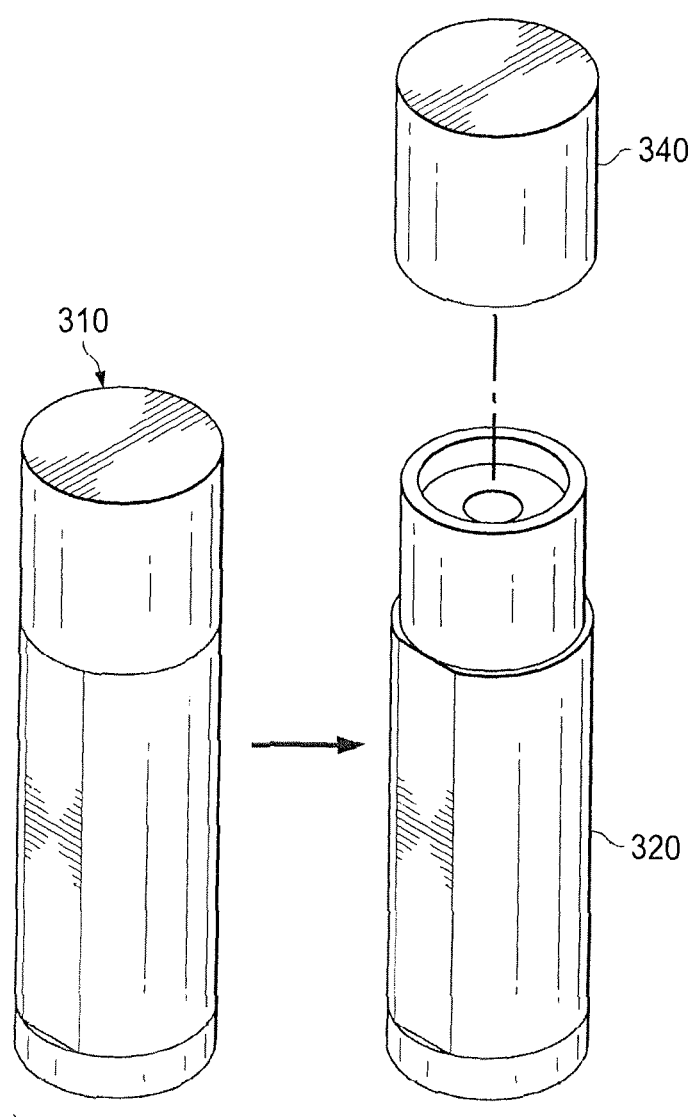
FIG. 4 is an elevational view of another embodiment of a solid stick-type applicator.
Figure 5:
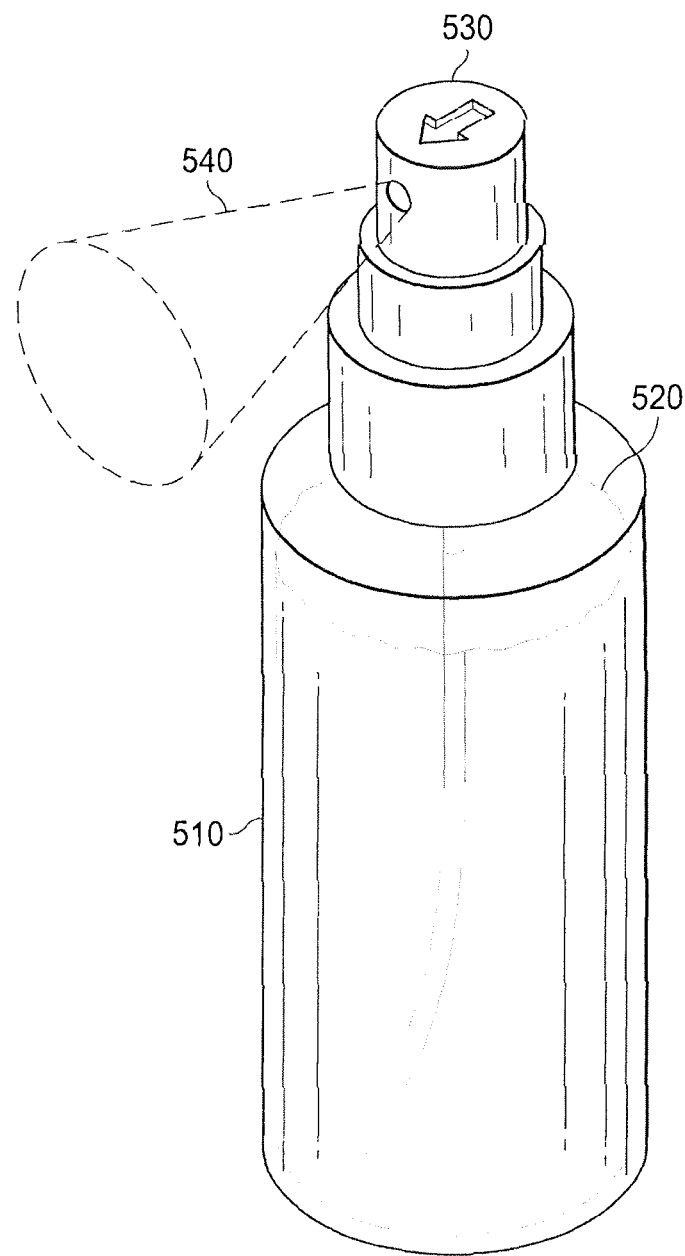
FIG. 5 is an elevational view of one embodiment of a spray bottle.

In one embodiment, the composition includes a therapeutically effective amount of an AMPK agonist for use as a topical medication for the treatment of one or more human medical conditions when applied with the use with (a) a roll-on applicator (e.g., FIG. 1) or (b) a pen-type (e.g., wick) applicator (e.g., FIG. 2), (c) a solid stick-type applicator (i.e. tube stick) similar to a deodorant applicator (e.g., FIG. 3), a solid stick-type applicator similar to a lip-balm type applicator (e.g., FIG. 4), and (d) a spray bottle (e.g., FIG. 5).

FIG. 1 is an elevational view of one embodiment of a roll-on applicator. The roll-on applicator embodiment has a container 110 configured to contain a quantity of medication (not shown) in liquid form. A roller 120 is captured in a receptacle at a dispensing end of its container, allowing it to rotate in any direction. Liquid medication (which may be a cream or gel) is conveyed on the surface of the roller from within the container to the skin, where it is applied. A cap (not shown) can cover the roller 120 when not in use to inhibit drying.

Figure 2:
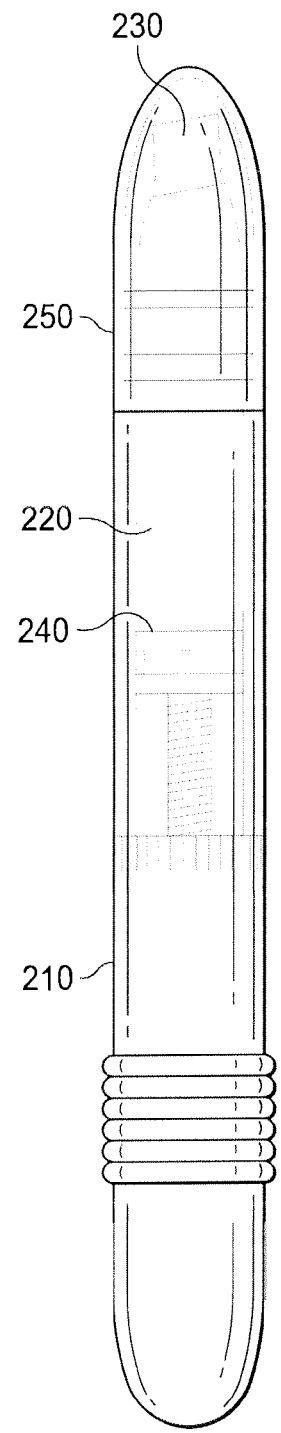
FIG. 2 is an elevational view of one embodiment of a pen-type applicator.

FIG. 2 is an elevational view of one embodiment of a pen-type applicator. The pen-type applicator embodiment has a body 210 configured to contain a quantity of medication (not shown) in liquid form in a reservoir 220 thereof. A wick 230 is in fluid communication with the reservoir 220. The medication is applied by applying pressure to the reservoir 220 using an actuator 240, whereupon the medication is forced into and through the wick 230, at which point it becomes available for application. A cap 250 can cover the wick 230 when not in use to inhibit drying.

Figure 3:
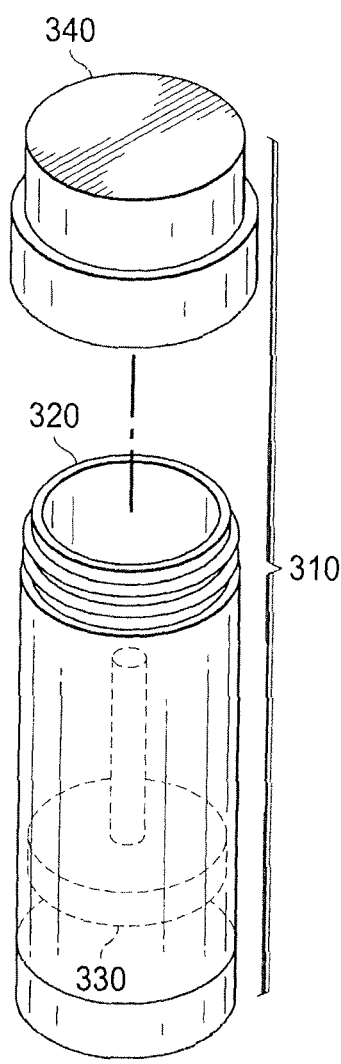
FIG. 3 is an elevational view of one embodiment of a solid stick-type applicator.

FIG. 3 is an elevational view of one embodiment of a solid stick-type applicator 310. The solid stick-type applicator embodiment has a container 320 configured to contain a quantity of medication (not shown) in solid form (often a very thick paste). An actuator 330 may be used to advance the medication until it protrudes from an end of the body 310. The medication may then be applied. A cap 340 can cover the exposed end of the medication to inhibit drying. In the embodiment of FIG. 3, the cap 340 screws onto and off of the container 320. FIG. 4 is an elevational view of another embodiment of a solid stick-type applicator in which the cap 340 is press-fit on the container 320.

FIG. 5 is an elevational view of one embodiment of a spray bottle. The spray bottle embodiment has a reservoir 510 configured to contain a quantity of medication 520 in liquid form. A spray head 530 is depressed, perhaps repeatedly, to cause the medication to be drawn up into it, where it is atomized and delivered as a spray 540 for application.

Figure 6:
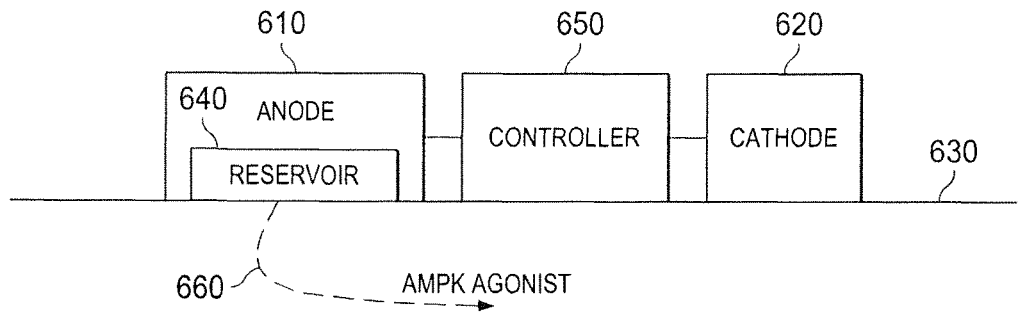
FIG. 6 is an elevational view of one embodiment of an iontophoretic transdermal system.

Another mechanism that may be employed to deliver a topical AMPK agonist is an iontophoretic transdermal system (FIG. 6). FIG. 6 is an elevational view of one embodiment of an iontophoretic transdermal system. As those skilled in the pertinent art understand, an iontophoretic system employs an anode 610 and a cathode 620 conductively coupled to the surface of skin 630. An ionized form of a medication 660 to be delivered by the system is located in a reservoir 640, typically associated with the anode 610. A controller 650 applies a mild voltage (e.g., three volts) across the anode 610 and the cathode 620, causing an electrical current to flow from the anode 610 to the cathode 620. Being ionized, the medication 660 bears the current and is transported transdermally, where it can take effect. In one embodiment, the controller 650 allows a patient to control when the voltage is applied and the medication is delivered. In one embodiment, such system is used with an ionized form of an AMPK agonist to deliver the AMPK agonist to treat pain, such as migraine. In another embodiment, another medication is combined with the AMPK agonist to provide a synergistic effect to treat pain.

In one embodiment, the system employs a therapeutically effective amount of an AMPK agonist as a topical medication for the treatment of one or more human medical conditions, when used in combination with electrical neuromodulation therapy. In a specific embodiment, the neuromodulation therapy employs closed-loop sensing of nerve signals. In another specific embodiment, the AMPK agonist consists of one or more of the following: resveratrol, metformin, 5-Aminoimidazole-4-carboxamide ribonucleotide (AICAR), berberine, epigallocatechin-3-gallate (EGCG), carnitine, R-Lipoic acid, quercetin, glucosamine, curcumin, anthocyanins, cannabinoids, genistein, astragalus, reishi, rooibos, creatine, gynostemma, apigenin, hydroxytyrosol, and baicalin. In yet another specific embodiment, the therapy is intended for use for the treatment of neuropathic, inflammatory, or nociceptive pain.

In one embodiment, the wound dressing incorporates a composition comprising a therapeutically effective amount of an AMPK agonist for use as a topical medication for the treatment of human or animal medical conditions, including relief from pain, itching, and inflammation, in combination with an antimicrobial agent. In a specific embodiment, the AMPK agonist consists of one or more of the following: resveratrol, metformin, AICAR, berberine, EGCG, carnitine, R-Lipoic acid, quercetin, glucosamine, curcumin, anthocyanins, cannabinoids, genistein, astragalus, reishi, rooibos, creatine, gynostemma, apigenin, hydroxytyrosol, and baicalin. In another specific embodiment, the antimicrobial agent consists of or contains one or more of the following: silver, gentamicin, and mafenide acetate.

Figure 7:
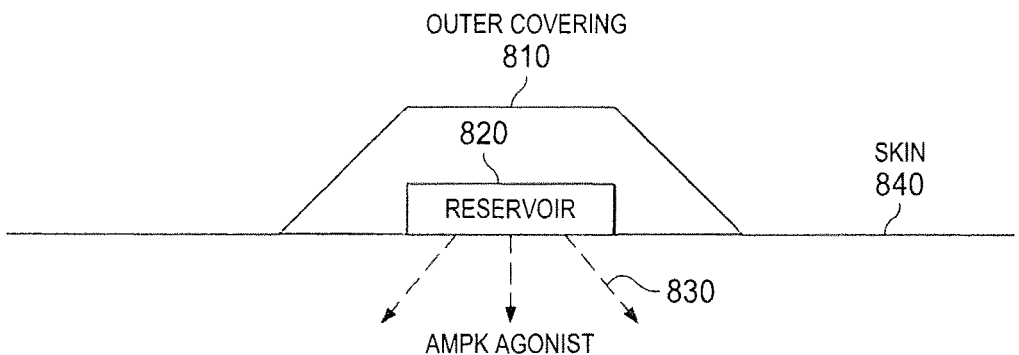
FIG. 7 is an elevational view of one embodiment of a transdermal patch.

In one embodiment, a therapeutically effective amount of an AMPK agonist is delivered by incorporation into a transdermal patch which is applied to the skin of the patient (FIG. 7). FIG. 7 is an elevational view of one embodiment of a transdermal patch having an outer covering 810 and a reservoir 820. The patch is applied to skin 830, at which point it begins to deliver an AMPK agonist 840 transdermally. Such application method is expected to enhance delivery of medication to areas of subcutaneous pain by minimizing loss of medication due to friction with clothing or surroundings. The transdermal patch may comprise an AMPK agonist and one or more other medications, which may act synergistically in treating the pain symptoms of a patient.

Figure 8:
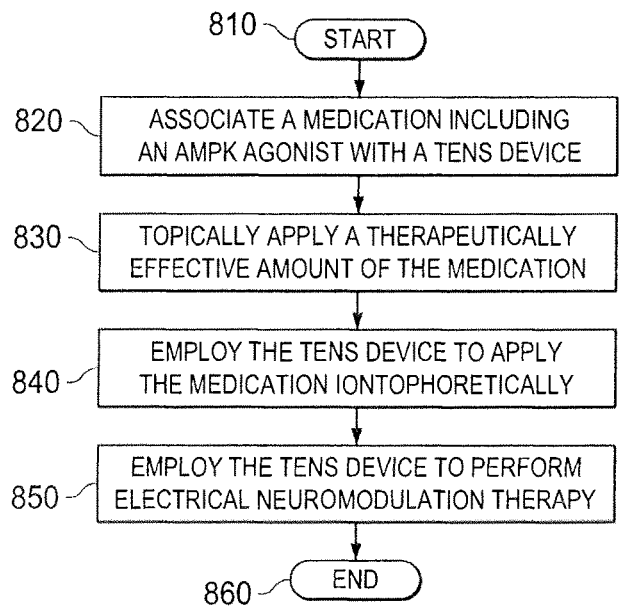
FIG. 8 is a flow diagram of one embodiment of an iontophoretic transdermal method.

FIG. 8 is a flow diagram of one embodiment of an iontophoretic transdermal method. The method begins in a start step 810. In a step 820, a medication including an AMPK agonist is associated with a TENS device. In a step 830, a therapeutically effective amount of the medication is topically applied. In a step 840, the TENS device is employed to apply the medication iontophoretically. In a step 850, the TENS device is employed to perform electrical neuromodulation therapy. The steps 840, 850 may be carried out concurrently, sequentially, or in an order determined by closed-loop sensing of nerve signals. The method ends in an end step 860.

Those skilled in the art to which this application relates will appreciate that other and further additions, deletions, substitutions and modifications may be made to the described embodiments.

What is claimed is:

1. A method of treating pain in a subject, the method comprising administering topically to the subject a therapeutically effective amount of a pharmaceutical composition consisting of:
   a 5'-adenosine monophosphate-activated protein kinase (AMPK) agonist;
   at least one inactive ingredient that affects at least one pharmaceutical composition characteristic selected from the group consisting of a texture, a viscosity, improved transdermal absorption efficacy, and a scent;
   methyl salicylate, and
   an antimicrobial agent.

2. The method of claim 1, wherein the pharmaceutical composition is administered using an application device configured to contain the pharmaceutical composition, wherein the at least one inactive ingredient eases topical application of the pharmaceutical composition by the application device.

3. The method of claim 2, wherein the application device is selected from the group consisting of a roll-on applicator, a pen-type applicator, a solid stick-type applicator, spray bottle, and a wound dressing.

4. The method of claim 1, wherein the AMPK agonist comprises at least one selected from the group consisting of metformin, 5-Aminoimidazole-4-carboxamide ribonucleotide (AICAR), berberine, epigallocatechin-3-gallate (EGCG), carnitine, R-Lipoic acid, quercetin, glucosamine, curcumin, anthocyanins, cannabinoids, genistein, astragalus, reishi, rooibos, creatine, gynostemma, apigenin, hydroxytyrosol, and baicalin.

5. The method of claim 1, wherein the at least one inactive ingredient is selected from the group consisting of water, mineral oil, glycerin, stearic acid, phenoxyethanol, panthenol, cetearyl alcohol, sodium hydroxide, sodium citrate, citric acid, dimethyl sulfoxide, pluronic lecithin organogel, and ethylparaben.

6. The method of claim 1, wherein the antimicrobial agent is selected from the group consisting of silver, gentamicin, and mafenide acetate.

7. The method of claim 1, wherein the subject has at least one disease selected from the group consisting of shingles, Post-Herpetic Neuralgia (PHN), gout, a migraine, trigeminal neuralgia, Complex Regional Pain Syndrome (CRPS), diabetic neuropathy, peripheral neuropathy, rheumatoid arthritis, an insect-related wheal, a urushiol-related rash, psoriasis, herpes simplex, atopic dermatitis, contact dermatitis, allergic dermatitis, a neurotrophic ulcer, a burn, fibromyalgia, rubeola, acne, itching, repetitive motion, blunt force trauma, a laceration, an abrasion, frostbite, and a puncture.

8. A method of treating pain in a subject, the method comprising administering topically to the subject a therapeutically effective amount of a pharmaceutical composition consisting of:
glucosamine;
at least one inactive ingredient that affects at least one pharmaceutical composition characteristic selected from the group consisting of a texture, a viscosity, improved transdermal absorption efficacy, and a scent;
an analgesic agent; and
an antimicrobial agent.

9. The method of claim 8, wherein the pain is associated with at least one disease selected from the group consisting of shingles, Post-Herpetic Neuralgia (PHN), gout, a migraine, trigeminal neuralgia, Complex Regional Pain Syndrome (CRPS), diabetic neuropathy, peripheral neuropathy, rheumatoid arthritis, an insect-related wheal, a urushiol-related rash, psoriasis, herpes simplex, atopic dermatitis, contact dermatitis, allergic dermatitis, a neurotrophic ulcer, a burn, fibromyalgia, rubeola, acne, itching, repetitive motion, blunt force trauma, a laceration, an abrasion, frostbite, and a puncture.

10. The method of claim 8, wherein the analgesic agent is methyl salicylate.

11. The method of claim 8, wherein the pharmaceutical composition is administered using an application device configured to contain the pharmaceutical composition, wherein the at least one inactive ingredient eases topical application of the pharmaceutical composition by the application device.

12. The method of claim 11, wherein the application device is selected from the group consisting of a roll-on applicator, a pen-type applicator, a solid stick-type applicator, spray bottle, and a wound dressing.

13. A method of treating shingles in a subject, the method comprising administering topically to the subject a therapeutically effective amount of a pharmaceutical composition consisting of:
glucosamine;
at least one inactive ingredient that affects at least one pharmaceutical composition characteristic selected from the group consisting of a texture, a viscosity, improved transdermal absorption efficacy, and a scent;
methyl salicylate; and
an antimicrobial agent.

14. The method of claim 13, wherein the at least one inactive ingredient is selected from the group consisting of water, mineral oil, glycerin, stearic acid, phenoxyethanol, panthenol, cetearyl alcohol, sodium hydroxide, sodium citrate, citric acid, dimethyl sulfoxide, pluronic lecithin organogel, and ethylparaben.

15. The method of claim 13, wherein the pharmaceutical composition is administered using an application device configured to contain the pharmaceutical composition, wherein the at least one inactive ingredient eases topical application of the pharmaceutical composition by the application device.

16. The method of claim 15, wherein the application device is selected from the group consisting of a roll-on applicator, a pen-type applicator, a solid stick-type applicator, spray bottle, and a wound dressing.

* * * * *